(12) United States Patent
Cuddeback et al.

(10) Patent No.: US 12,186,341 B1
(45) Date of Patent: Jan. 7, 2025

(54) PHYTOCHEMICAL/ NUTRACEUTICAL COMPOSITION FOR MULTIMODAL PROPHYLAXIS AGAINST AND TREATMENT OF VIRAL AND BACTERIAL INFECTION AND INFLAMMATION

(71) Applicant: David A Cuddeback, Kirkwood, NY (US)

(72) Inventors: David A. Cuddeback, Kirkwood, NY (US); Thomas J. Lynch, Elverson, PA (US)

(73) Assignee: David A. Cuddeback, Kirkwood, NY (US)

( * ) Notice: Subject to any disclaimer, the term of this patent is extended or adjusted under 35 U.S.C. 154(b) by 0 days.

(21) Appl. No.: 17/682,300

(22) Filed: Feb. 28, 2022

Related U.S. Application Data

(63) Continuation-in-part of application No. 16/848,393, filed on Apr. 14, 2020, now abandoned.

(51) Int. Cl.

| | |
|---|---|
| *A61K 36/00* | (2006.01) |
| *A61K 9/00* | (2006.01) |
| *A61K 9/48* | (2006.01) |
| *A61K 31/05* | (2006.01) |
| *A61K 31/12* | (2006.01) |
| *A61K 31/198* | (2006.01) |
| *A61K 31/202* | (2006.01) |
| *A61K 31/352* | (2006.01) |
| *A61K 31/355* | (2006.01) |
| *A61K 31/375* | (2006.01) |
| *A61K 31/4525* | (2006.01) |
| *A61K 33/30* | (2006.01) |
| *A61K 36/15* | (2006.01) |
| *A61K 36/185* | (2006.01) |
| *A61K 36/233* | (2006.01) |
| *A61K 36/28* | (2006.01) |
| *A61K 36/324* | (2006.01) |
| *A61K 36/328* | (2006.01) |
| *A61K 36/537* | (2006.01) |
| *A61K 36/74* | (2006.01) |
| *A61K 36/82* | (2006.01) |

(52) U.S. Cl.
CPC ............ *A61K 33/30* (2013.01); *A61K 9/0053* (2013.01); *A61K 9/48* (2013.01); *A61K 31/05* (2013.01); *A61K 31/12* (2013.01); *A61K 31/198* (2013.01); *A61K 31/202* (2013.01); *A61K 31/352* (2013.01); *A61K 31/355* (2013.01); *A61K 31/375* (2013.01); *A61K 31/4525* (2013.01); *A61K 36/15* (2013.01); *A61K 36/185* (2013.01); *A61K 36/233* (2013.01); *A61K 36/28* (2013.01); *A61K 36/324* (2013.01); *A61K 36/328* (2013.01); *A61K 36/537* (2013.01); *A61K 36/74* (2013.01); *A61K 36/82* (2013.01)

(58) Field of Classification Search
CPC ..... A61K 31/375; A61K 31/355; A61K 33/30
See application file for complete search history.

(56) References Cited

U.S. PATENT DOCUMENTS

| | | | |
|---|---|---|---|
| 6,407,090 B1 * | 6/2002 | Fliss ...................... | A61K 31/40 514/188 |
| 10,568,866 B1 * | 2/2020 | Niedzwiecki ........ | A61K 31/375 |
| 2006/0057186 A1 * | 3/2006 | Heller .................. | A61K 36/232 424/641 |
| 2013/0224298 A1 * | 8/2013 | Von Drachenfels ... | A61K 36/87 424/766 |
| 2015/0190455 A1 * | 7/2015 | Azizkhani .......... | A61K 36/9068 424/756 |

FOREIGN PATENT DOCUMENTS

| | | | | |
|---|---|---|---|---|
| CN | 103284964 | A * | 9/2013 | |
| CN | 111000976 | A * | 4/2020 | |
| FR | 2853246 | A1 * | 10/2004 | ........... A23L 33/105 |
| HU | 9603193 | A2 * | 11/1998 | |

OTHER PUBLICATIONS

Verma et al, Oral zinc sulphate therapy in acne vulgaris: a double-blind trial. Acta dermato-venereologica, (1980) vol. 60, No. 4, pp. 337-340 (Year: 1980).*
Tallaride, Quantitative methods for assessing drug synergism, Genes & Cancer 2(11) 1003-1008, 2011 (Year: 2011).*
Raskin et al, Can an apple a day keep the doctor away, Current Pharmaceutical Designs, 2004, 10: 3419-3429 (Year: 2004).*
Zhou et al, Vitamin D3 pretreatment protects against lipopolysaccharide-induced early embryo loss through its anti-inflammatory effects. American Journal of Reproductive Immunology (2017), vol. 77, No. 3, pp. e12620 (Year: 2017).*
Erbach et al, Does biotin deficiency play a role in IBD pathogenesis Preliminary results of a cross-sectional study. United European Gastroenterology Journal, (Oct. 2021) vol. 9, No. Suppl 8, pp. 391. Abstract No. P0231 (Year: 2021).*
Badr et al, Anti-inflammatory and anti-cancer effects of β-carotene, extracted from Dunaliella bardawil by milking. Journal of Food, Agriculture & Environment (2014), vol. 12, No. 3/4, pp. 24-31 (Year: 2014).*
Hikal, An Overview of Pomegranate Peel: A Waste Treasure for Antiviral Activity. Tropical Journal of Natural Product Research, (Jan. 2022) vol. 6, No. 1, pp. 15-19 (Year: 2022).*

(Continued)

*Primary Examiner* — Qiuwen Mi

(57) ABSTRACT

A phytochemical and nutraceutical composition and method for protection against a wide spectrum of viral and bacterial infections, including Covid-19, and for treatment of established infection and infectious inflammation. The composition includes a novel combination of vitamin, mineral, nutraceutical and phytochemical supplements. The composition of supplements and method may be compounded as a pill, tablet, powder, capsule or liquid be taken orally one or more times per day. Vitamin C and vitamin E along with zinc complexed with pyrithione or citrate are used in conjunction with nutraceuticals and phytochemicals provided, respectively, as immune boosters and antiviral agents along with anti-inflammatory nutraceuticals and phytochemicals.

12 Claims, No Drawings

(56) References Cited

OTHER PUBLICATIONS

Song, Tea catechins as a potential alternative anti-infectious agent. Expert review of anti-infective therapy, (Jun. 2007) vol. 5, No. 3, pp. 497-506 (Year: 2007).*

Tao et al, Evaluation of the anti-inflammatory properties of the active constituents in Ginkgo biloba for the treatment of pulmonary diseases. Food & function (Apr. 17, 2019), vol. 10, No. 4, pp. 2209-2220, 12 p (Year: 2019).*

Jambi et al, Potential antioxidant, anti-inflammatory and gastroprotective effect of grape seed extract in indomethacin-induced gastric ulcer in rats. International Journal of Pharmacology (2019), vol. 15, No. 2, pp. 209-218 (Year: 2019).*

Sochocka et al, Hampering Herpesviruses HHV-1 and HHV-2 infection by extract of Ginkgo biloba (EGb) and its phytochemical constituents. Frontiers in Microbiology (2019), vol. 10, Number October, 32 refs (Year: 2019).*

Lee et al, Evaluation of green tea extract as a safe personal hygiene against viral infections. Journal of biological engineering, (2018) vol. 12, pp. 1 (Year: 2018).*

Mustafa et al, Comparison of Phytochemicals, Antioxidant and Anti-Inflammatory Properties of Sun-, Oven- and Freeze-Dried Ginger Extracts. Foods (Basel, Switzerland), (Oct. 6, 2019) vol. 8, No. 10 (Year: 2019).*

Yuvaraj et al, Anti-inflammatory and preventive activity of white mulberry root bark extract in an experimental model of pancreatitis. Journal of traditional and complementary medicine, (Oct. 2018) vol. 8, No. 4, pp. 497-505 (Year: 2018).*

Thi et al, Anti-cancer and anti-inflammatory activities of aronia (*Aronia melanocarpa*) leaves. Asian Pacific Journal of Tropical Biomedicine (2018), vol. 8, No. 12, pp. 586-592 (Year: 2018).*

Handeland, Black chokeberry juice (*Aronia melanocarpa*) reduces incidences of urinary tract infection among nursing home residents in the long term—a pilot study. Nutrition research (New York, N.Y.), (Jun. 2014) vol. 34, No. 6, pp. 518-525 (Year: 2014).*

* cited by examiner

PHYTOCHEMICAL/ NUTRACEUTICAL COMPOSITION FOR MULTIMODAL PROPHYLAXIS AGAINST AND TREATMENT OF VIRAL AND BACTERIAL INFECTION AND INFLAMMATION

CROSS-REFERENCE TO RELATED APPLICATIONS

This application is a continuation-in-part of utility application Ser. No. 16/848,393 filed Apr. 14, 2020 by the same inventors.

BACKGROUND OF THE INVENTION

Field of the Invention

This invention relates to phytochemical/nutraceutical compositions, products and methods that include multimodal prophylaxis against and treatment of viral and bacterial infections and inflammations, especially in human beings.

Description of Related Art

Nutraceuticals are: A) Dietary Supplements, such as vitamins, minerals, herbs, amino acids, enzymes, organ tissues or metabolites and, B) Functional Foods, defined in a position statement by the Academy of Nutrition and Dietetics: Functional Foods. Kristi Crowe, Coni Francis, J *Acad Nutr Diet.* 2013; 113:1096-1103, as "whole foods along with fortified, enriched, or enhanced foods that have a potentially beneficial effect on health when consumed as part of a varied diet on a regular basis at effective levels based on significant standards of evidence." Examples would be "the antioxidant vitamins in orange juice, isoflavones in soy-based foods, and prebiotics and probiotics in yogurt." In all such instances, the antioxidant or other functional ingredient is contained within an intact, whole food.

Phytonutrients, defined by the NIH/National Cancer Institute, "are organic components of plants thought to promote human health. Fruits, vegetables, grains, legumes, nuts and teas are rich sources of phytonutrients. Unlike the traditional nutrients (protein, fat, carbohydrates, vitamins, and minerals), phytonutrients are not 'essential' for life, so some people prefer the term Phytochemical."

Phytochemicals, within the parent plant, help the plant resist microbial attack by fungi, bacteria and viruses. Phytochemicals are further defined by Liviuta Budisan et al; Int J Mol Scvi. 2017 June; 18 (6): 1178 as, "natural compounds synthesized as secondary metabolites in plants, representing an important source of molecules with a wide range of therapeutic applications." Budisan et al. explains further that: "these natural agents are important regulators of key pathological processes/conditions, including cancer, as these natural agents are able to modulate the expression of coding and non-coding transcripts with an oncogenic or tumor suppressor role."

Phytochemicals are also known to have multiple antiviral effects in vitro and multiple anti-inflammatory effects in vitro and in vivo.

For phytochemicals to be most effective in their use, they must be extracted in concentrated form from the parent plant.

Chemical classifications of the family of phytochemicals are all slightly different. Polyphenols are phytochemicals, found largely in fruits, vegetables, tea, coffee, chocolates, legumes, cereals, and beverages. There are over 8000 polyphenols identified in nature and their main function is antioxidant and other significant health benefits.

Many effective drugs have come originally from phytochemical sources. A selected few examples follow: Willow bark was used more than 3500 years ago as an analgesic and antipyretic, although those terms were not used at the time. About 1897, Felix Hoffman discovered its active component to be the phytochemical salicin, which inspired his synthesis of salicylic acid (aspirin). Atropine first came from the *belladonna* plant (aka nightshade) and is now used to decrease respiratory secretions during surgery, to treat poisoning by certain cholinergic nerve agents and as the first line treatment for symptomatic bradycardia in the emergency department. Paclitaxel was isolated from the English Yew tree in 1971 and has since been used to treat ovarian, breast, and non-small cell lung cancer. In 1928, Alexander Fleming discovered the first antibiotic, penicillin, in mold of the genus *Penicillium*.

There is renewed interest in phytochemicals because of more recent research that has demonstrated antiviral and antibacterial efficacy of various phytochemicals in numerous in vitro experiments and especially now because of the prophylactic and therapeutic quandary presented by the SARS COV-2 pandemic. The COVID-19 oral antiviral pills recently introduced by Pfizer, Paxlovid (ritonavir), and by Merck, Lagevrio (molnupiravir), were first discovered in in vitro research, then confirmed in in vivo (human) clinical trials. It is a common research pattern that positive results in vitro often become positive results in vivo (humans and animals).

Phytochemicals are not food, vitamins or minerals per se. They are plant chemicals with multiple, evolved non-nourishment purposes, particularly plant defense. Of note, their molecular structures can bear resemblance to laboratory chemicals invented for human defense.

Before modern pharmaceuticals, mankind depended on natural substances for medical purposes which included, but were not limited to, relieving pain, enhancing sexual and other performance, enhancing sleep, enhancing bowel function, healing wounds, decreasing respiratory difficulty, stopping blood loss, halting the progress of illness and augmenting general wellbeing. Such natural substances included, but were not limited to, vegetables, herbs, roots, flowers, tree barks and certain animal organs and tissues. A key target of the use of natural substances was abatement of the combination of pain, swelling and redness in any area of the body, a combination which by the 16th century came to be known as inflammation. At that time and before, inflammation was an important target for treatment with natural substances because it was well recognized that inflammation could progress to worse, morbidity or death. Although allergic or purely traumatic injury can also cause inflammation, in the 19th century it was discovered that bacterial infection was a chief and more dangerous cause. In the 20th century, knowledge of the causes of inflammation expanded to include viral and fungal infections.

In our time, natural substances have evolved to include isolated atoms known as minerals, isolated biomolecules known as vitamins and purified extracts from any of the above mentioned, historical sources of natural substances. There is a large variety of such modern natural substances, which in modern pill, tablet, liquid, powder or capsule form are now known as dietary or health supplements, or nutraceuticals. Nutraceuticals and phytochemicals are currently used for essentially the same array of purposes as those throughout history, but now also for fortification of the immune system against primary acquisition of infection, i.e. prophylaxis, and for fortification of the immune system's ability to defeat infection once it is established.

Modern antibacterial and antiviral vaccines are generally effective against only the bacterial or viral pathogen from which they were pharmaceutically derived, not a range of bacteria or viruses. Modern (antibacterial) antibiotics for use after infection has already occurred are typically quite effective against some range of bacteria. Historically however, antiviral medications for use after viral infection has already occurred, work against only a specific virus, have minimal and even questionable effectiveness and also have severe time constraints on their uses.

A small variety of available supplements are targeted at overall fortification of the innate immune system, with the intent to prevent or mollify a variety of viral and bacterial infections such that no infection occurs, or that its symptoms and physiologic effects may be restricted to the minimal and the brief. These supplements go by such labels as Immune Boost, Immune Health and others, and many, if not most, are composed of a single active ingredient, and none claims both immune fortification and inclusion of a known anti-inflammatory substance.

What is needed is a novel and optimal combination of immune fortifying ingredients, each of which works by a different mechanism to prevent, mollify and treat a wide range of viral and bacterial infections (hereafter termed wide-spectrum anti-infectious), and another ingredient or ingredients which is/are anti-inflammatory, in the event that some degree of infectious inflammation becomes established.

Since whole-food nutraceuticals are an inefficient and minimally effective source of immune-fortifying, antiviral and anti-inflammatory ingredients, what is needed is a novel and unique combination of extracted phytochemicals whose wide-spectrum prophylactic effect against infection is compounded by its ability to treat already established infection and infectious inflammation, such that its overall prophylactic and therapeutic effects synergistically equal more than the sum of its parts, as does the fortuitous combination of vitamin C+thiamine+hydrocortisone in reversal of sepsis, a severely life-threatening condition which can follow routine infection with a virus or bacterium.

Phytochemical extracts do not exist in nature. Further, any extract of a plant contains not one phytochemical but an array of phytochemicals. The above combination of vitamin C+thiamine+hydrocortisone used for sepsis is referred to as a clinical cocktail. Clinical cocktails are little used in medicine. Instead, the tradition in Western medicine is one clinical drug for one clinical problem, which is not always successful. The purpose of a clinical cocktail is to overwhelm the clinical problem by causing multiple corrective effects at once. To protect against viral infection, we propose a combination three nutraceuticals that support the innate immune system (zinc, vitamin C and vitamin E) plus an unnatural combination (cocktail) of seven antiviral phytochemical extracts from seven different plants, wherein each extract itself contains its own sub-array of antiviral phytochemicals. Representative literature references citing the in vitro antiviral and/or antibacterial efficacy of the phytochemical extracts we propose include those for extracted fulvic acid, *Radix bupleuri* extract, *Uncaria tomentosa* extract, pomegranate extract, black elderberry extract, sage extract, and *echinacea* extract.

The invention utilizes a phytochemical cocktail approach to prevent or treat health-threatening inflammation caused by an established viral or bacterial infection. To protect against infectious inflammation, the invention includes a method and a composition having a combination of two anti-inflammatory nutraceuticals (omega-3 fatty and-lipoic acid) plus an unnatural combination (cocktail) of eight anti-inflammatory phytochemical extracts from eight different plants, wherein each extract itself contains its own sub-array of anti-inflammatory phytochemicals. Representative literature references provided in an information disclosure statement citing the in vitro and/or in vivo anti-inflammatory efficacy of the phytochemical extracts contained in the invention include those for *Boswellia serrata* extract, maritime pine bark extract, *Uncaria tomentosa* extract, *Commiphora myrrha* extract, resveratrol, alpha-lipoic acid, curcumin extract with piperine, green tea extract, Omega-3 fatty acids, and cannabidiol.

Among the obvious benefits of virology research is the elucidation of viral structures, and the mechanisms of virus-to-host-cell-attachment, virus entry and replication and viral budding. Among the obvious benefits of other medical research is elucidation of the numerous mechanisms of cell function and the numerous mechanisms of normal versus maladaptive inflammation. The nutraceuticals contained in the proposed antiviral cocktail in the invention method and composition support numerous facets of the innate immune system, and the phytochemicals contained therein are known to combat many or most of the mechanisms of viral infection and replication.

The nutraceuticals and phytochemicals contained in the anti-inflammatory cocktail described herein are known in the literature to inhibit or block a key set of chemical mediators of inflammation (e.g. cytokines,) that cause serious viral inflammation, and notably those that cause cytokine storm in COVID-19. These mediators include IL-1B, IL-6, NF-kappa B, leukotrienes, TNF-alpha and the enzyme, human leukocyte elastase, believed to cause lung tissue destruction in emphysema.

In addition to cytokines, oxygen free radicals are also known to be key players in inflammatory processes. So too, inflammatory processes in the vascular endothelium cause endotheliitis in COVID-19, which enables thrombogenesis and which in turn creates multiple clots that cause stroke, heart attack and renal failure. Another facet of the invention anti-inflammatory phytochemical cocktail, with its inherent subarrays of other phytochemicals, is that many of the phytochemicals contained therein also have antioxidant and/or antithrombotic effects.

Still another facet of the invention method and compositions enclosed, is that desired effects, whether antiviral, anti-inflammatory, antioxidant or antithrombotic, should be potentiated by the effects of each component compounding the effects of the others. This has been found for pomegranate rind extract and punicalagin when co-administered with zinc in its virucidal activity against both herpes simplex virus (HSV) and acyclovir-resistant HSV. Of the multiple, possible mutual potentiations among our phytochemicals, synergy between two or more is also possible, synergy in which the combined effect of two or more is significantly greater than the sum of their individual effects. Synergy has been found for the anti-inflammatory effect of the co-administration of *Commiphora myrrha* extract with *Boswellia* extract.

A common feature of laboratory-invented antiviral medications (e.g. oseltamivir & zanamivir) used against influenza virus is that strains of influenza (e.g. H1N1 and H3N2) rapidly develop resistance to the medication and thereafter become ineffective in certain populations. A curiosity of several of our proposed anti-infective phytochemicals is that even after multiple passes in vitro, the viruses against which they were being tested failed to develop resistance to the phytochemicals, whereas the same number of in vitro passes caused significant viral resistance against laboratory-invented antiviral medications. There is as yet no explanation for this advantage of phytochemicals.

By and large, research has not tested the combination of even two co-administered phytochemicals for their anti-infectious or anti-inflammatory effects, let alone a cocktail of 3 or more. An unexpected result thereof, or perhaps a foregone conclusion, should be that since each of these phytochemical extracts has been shown to be effectively antiviral against one or more viruses in vitro, then a cocktail of all seven extracts should be even more antiviral against any one virus, and effectively antiviral against a much wider range of different viruses.

SUMMARY OF THE INVENTION

A novel combination of vitamin, mineral and herbal or other natural, organic supplements (phytochemicals) for protection against a wide spectrum of viral and bacterial infections, and for treatment of established infection and infectious inflammation. The composition of vitamin, mineral and phytochemical supplements is to be compounded as a pill, tablet, powder, capsule or liquid to be taken orally one or more times per day, or as parenteral liquid.

Among the possible innate immune system-supporting vitamins to be used are vitamins C and E. The mineral to be used is zinc complexed with citrate, pyrithione, or the amino acid methionine, or other cofactor, in order to increase zinc's bioavailability.

Phytochemicals provided herein as immune boosters and/or antiviral agents to be combined as a composite in one vehicle include *echinacea* purpura extract, extracted fulvic acid, black elderberry extract, sage extract, Cat's Claw extract (*Uncaria tomentosa*), pomegranate extract, *Radix bupleuri* extract (saikosaponins) and cannabidiol (CBD).

The anti-inflammatory phytochemicals and nutraceuticals to be used are *Boswellia serrata* extract, maritime pine extract, Cat's Claw extract (*Uncaria tomentosa*), green tea extract, resveratrol, curcumin with piperine, alpha lipoic acid, *Commiphora myrrha* extract, cannabidiol (CBD) and the omega-3 fatty acids, DHA and EPA. Methods of using these compositions of vitamins, minerals, herbs and other organic substances and compositions are also disclosed herein. The amount of each individual supplement substance may be varied significantly.

An object of the invention is to provide compositions of phytochemical extracts and nutraceuticals to fortify the human or companion animal immune system in a way that prevents a wide spectrum of known or new strains of viruses and bacteria from starting a new infection in the host.

Another object of the invention is to provide compositions of phytochemical extracts and nutraceuticals to fortify the human or companion animal immune system in a way that permits nascent viral or bacterial infection, once established, to be treated and defeated before the infection can cause serious and/or widespread systemic symptoms and effects, or to minimize such symptoms to a life non-threatening level.

Another object of the invention is to provide compositions of phytochemical extracts and nutraceuticals that prevent or limit inflammation, especially in the lungs, in which virally or bacterially induced inflammation causes arteriolar and capillary leakage and resultant pulmonary edema, excess mucus secretion, possible severe bronchoconstriction and, in the worst case, acute respiratory distress syndrome (ARDS) with airway collapse, any of which phenomena can compromise pulmonary function to the point of fatal respiratory failure.

Another object of the invention is to provide compositions of anti-infective (antiviral and antibacterial) phytochemical extracts and nutraceuticals, already established to be safe for consumption that can be taken electively before anticipated viral exposure, prophylactically on a daily basis if desired, or therapeutically at the start of early viral symptoms.

Another object of the invention is to provide compositions of anti-inflammatory phytochemical extracts and nutraceuticals, already established to be safe for consumption that can be taken electively before anticipated viral exposure, prophylactically on a daily basis if desired, or therapeutically at the start of early viral symptoms.

Another object of the invention is to prevent or limit development of virally induced secondary bacterial infection/inflammation, or vice versa, especially in the lungs. An overall object of the invention is to help flatten the viral epidemic curve of yearly Influenza, and that of any new viral epidemic. Other features and advantages of the present invention will become apparent to those of skill in the art to consideration of the ensuing description and the appended claims.

DETAILED DESCRIPTION OF THE INVENTION

For the purposes of this specification, the word "nutraceutical", refers to a food item, or a part of a food item, that offers medical health benefits, including prevention and/or treatment of disease. More particularly, a nutraceutical is a material that is:
a. a dietary supplement containing a nutritive bioactive compound; or
b. a biologically active process or process material derived from a vitamin, mineral, and herbal/organic supplements plant, fungus, and animal, or a portion thereof; where the precise composition of the biologically active process or unprocessed material may be undetermined. The word phytochemical refers to non-nutritive organic components of plants that are thought to promote human health. Unlike the traditional nutrients (protein, fat, carbohydrates, vitamins and minerals), phytochemicals are not essential for life, but have a wide range of therapeutic applications. Phytochemicals, within the parent plant, help it resist microbial attack by fungi, bacteria, and viruses.

Examples of a biologically active process material may include a finely chopped, powdered, pureed, or cooked material derived from plant or animal tissue, or an extract of plant or animal tissue. These agents are useful for accelerating improved immune function; and they include extracts from various plants and mixtures thereof.

A novel and unique combination of vitamin, mineral and herbal/organic supplements (phytochemicals and nutraceuticals) in one formulary forming one or more compositions and methods for the purpose of fortifying the innate (cellular) and adaptive (hormonal) components of the immune system against bacterial and viral infection, and their propagation, transmission and effects.

Also included in the formulary compositions are two or more natural, herbal or other organic anti-inflammatory substances for the suppression of tissue inflammation, especially in the lungs. The formulary thereby provides multimodal nutraceutical and phytochemical protection against acquisition of infection and against deleterious effects of inflammation in the lungs. The formulary is available in both oral and parenteral forms.

In one preferred embodiment, the formulary composition contains:
25 mg zinc in any of its pyrithione, citrate, gluconate, picolinate, acetate, sulfate or orotate forms, or with the cofactor methionine.
1000 mg vitamin C
200 mg vitamin E
Two or more of the following anti-infectious nutraceuticals:
1000 mg fulvic acid
800 mg *Echinacea purpura*
400 mg Sage extract (*Salvia officinalis*)
300 mg Cat's Claw extract (*Uncaria tomentosa*)
200 mg Black Elderberry extract (*Sambucus nigra*) or 200 mg American Elderberry extract (*Sambucus canadensis*); and
Two or more of the following anti-inflammatory nutraceuticals:
1000 mg Omega-3 fatty acids, eicosapentanoic acid (EPA) and docosahexanoic acid (DHA).
400 mg Curcumin, including its presence in turmeric powder
300 mg Green Tea extract polyphenols.
200 mg gum resin of *Boswellia serrata*, containing its most anti-inflammatory moiety, 3-acetyl-11-keto-β-boswellic acid (AKBA)
200 mg Resveratrol
100 mg of Pycnogenol, extract of pine bark (*Pinus maritima*)

Any of the listed anti-infectious nutraceuticals permutated with any of the listed anti-inflammatory and, in term, combined with the Zinc and Vitamin C or E, will confer five levels of anti-infectious protection, including white blood cell fortification and activation, virucidal-bactericidal activity, enhancement of antibody production, anti-oxidant activity and anti-inflammatory activity. The oral formulary, capsule or other, is enteric-coated to prevent breakdown by gastric acid and permit delivery of unaltered nutraceuticals to the duodenum for absorption.

EXAMPLES OF EFFECTIVE COMPOSITIONS AND METHODS OF THE INVENTION OF ONE PREFERRED EMBODIMENT

Example 1

1. A nutraceutical composition in capsule or other oral form for preventing or mollifying viral or bacterial infection, and also for preventing or mollifying viral or bacterial tissue inflammation consisting of:
an effective amount of vitamin C;
an effective amount of vitamin E;
an effective amount of zinc;
effective amounts of wide-spectrum anti-infectious phytochemicals; and
effective amounts of an anti-inflammatory nutraceutical and phytochemicals.

Example 2

2. The composition of example 1, wherein an effective amount of wide-spectrum anti-infectious phytochemicals include an effective amount of five or more of the following:
extracted fulvic acid; *Radix bupleuri* extract; *Echinacea purpura* extract; sage extract; pomegranate extract; *Uncaria tomentosa* extract; Black Elderberry extract or American Elderberry extract.

Example 3

3. The composition of example 1, wherein an effective amount of anti-inflammatory nutraceuticals and phytochemicals include an effective amount of two or more of the following:
Nutraceuticals Omega-3 fatty acids; eicosapentanoic acid (EPA) and docosahexanoic acid (DHA); and
five or more of the following anti-inflammatory phytochemicals:
*Boswellia serrata* extract containing 3-acetyl-11-keto-beta-boswllic acid (AKBA); Maritime pine bark extract (*Pinus maritima*); *Unicaria tomentosa* extract; *Commiphora myrrha* extract; Resveratrol; Curcumin extract with piperine; green tea extract; and Cannabidiol.

Example 4

4. The composition of example 1, wherein an effective amount of anti-infectious phytochemicals and an effective amount of anti-inflammatory nutraceuticals and phytochemicals include:
Five or more of the following anti-infectious phytochemicals:
fulvic acid extract; *Radix bupleuri* extract;
*Echinacea purpura*; sage extract; Cats Claw extract (*Uncaria tomentosa*); Black Elderberry extract or American Elderberry, pomegranate extract and
two or more of the following anti-inflammatory nutraceuticals:
Omega-3 fatty acids; eicosapentanoic acid (EPA) and docosahexanoic acid (DHA); and
Five or more of the following anti-inflammatory phytochemicals:
Curcumin extract with piperine; Green Tea extracts; extract containing 3-acetyl-11-keto-beta-boswellic acid (AKBA); resveratrol; *Commiphora myrrha* extract; *Uncaria tomentosa*; and maritime pine bark extract Example 5

5. The composition of example 4, wherein:
zinc in any of its pyrithione, citrate, gluconate, picolinate, sulfate, acetate, or orotate forms.

Example 6

6. The composition of example 4, wherein:
zinc with the cofactor of methionine.

Example 7

7. The composition of example 1, wherein:
the effective amount of vitamin C is 1000 mg;
the effective amount of vitamin E is 200 mg.

Example 8

8. The composition as in example 5, wherein:
effective amount of zinc in any of its pyrithione, citrate, gluconate, picolinate, acetate, sulfate, orotate forms is 25 mg.

Example 9

9. The composition as in example 5, consisting of:
Five or more of the following anti-infectious phytochemicals and effective amounts:
   1000 mg of extracted fulvic acid;
   800 mg *Echinacea purpura*;
   800 mg sage extract (*Salvia officinalis*);
   400 Mg Cat's Claw extract (*Uncaria tomentosa*);
   200 mg Black Elderberry extract (*Sambucus nigra*) or 200 mg American Elderberry extract (*Sambucus canadensis*); 400 mg pomegranate extract; 400 mg *Radix bupleuri* extract.

Example 10

10. The composition in example 9, consisting of:
two or more of the following anti-inflammatory nutraceuticals and effective amounts:
   1000 mg Omega-3 fatty acids; eicosapentanoic acid (EPA) and docosahexanoic acid (DHA); 200 mg Alpha-lopoic acid;
And five or more of the following anti-inflammatory phytochemicals:
   400 mg Curcumin extract with piperine;
   300 mg Green Tea extract;
   800 mg of *Boswellia serrata* extract, containing its most anti-inflammatory moiety, three-acetyl-11-keto-beta-boswellic acid (AKBA);
   200 mg Resveratrol;
   100 mg of extract of Maritime pine bark (*Pinus maritima*);
   400 mg *Commiphora myrrha* extract; and
   400 mg *Unicaria tomentosa* extract.

Example 11

11. A method employing the composition recited in example 10, to prevent or limit development of virally induced infections and inflammation comprising the steps of:
   a) preparing the composition of example 10 for human consumption;
   b) processing composition prepared for human consumption recited in example 10 in tablet, powder, pill, capsule or liquid to be taken orally; and
   c) administering the processed composition recited in example 10 to a human being periodically.

Example 12

12. A method for treating a patient having symptoms caused by a viral or bacterial infection and related inflammation, including Covid-19, comprising the step of administering a nutraceutical and phytochemical composition to the patient, said nutraceutical portion of the composition consisting of vitamin C, vitamin E, and zinc in any of its pyrithione, citrate, gluconate, picolinate, sulfate, acetate, or orotate forms and appropriate nutraceutical and phytochemical components for preventing or reducing viral and bacterial infections and inflammations, wherein an effective amount of anti-infectious phytochemicals and an effective amount of anti-inflammatory nutraceuticals and phytochemicals include five or more of the following anti-infectious phytochemicals:
   a) fulvic acid; *Echinacea purpura* extract; sage extract; *Uncaria tomentosa* extract; Black Elderberry extract or American Elderberry extract; pomegranate extract; and *Radix bupleuri* extract; and
two or more of the following anti-inflammatory nutraceuticals:
   b) Omega-3 fatty acids; eicosapentanoic acid (EPA) and docosahexanoic acid (DHA}; and Alpha-lipoic acid; and
five or more of the following anti-inflammatory phytochemicals:
   c) Curcumin extract with piperine; green tea extract; *Boswellia serrata* extract, containing three-acetyl-11-keto-beta-boswellic acid (AKBA); resveratrol; *Commiphora myrrha* extract; *Uncaria tomentosa* extract; extract of maritime pine bark; green tea extract; and
   d) Cannabidiol (CBD).

Example 13

13. The method as in example 12, wherein, the step of adding a nutraceutical composition administering nutraceutical composition containing zinc with the cofactor of methionine.

Example 14

14. The method as in example 13, wherein the step of administering the nutraceutical composition in the effective amount of vitamin C 1000 mg; effective amount of vitamin E is 200 mg; and the effective amount of zinc is 25 mg

Example 15

15. The method as in example 14, wherein the step of administering the effective amount of anti-infectious nutraceuticals in the composition include two or more of the following anti-infectious phytochemicals:
   a) 1000 mg fulvic acid extract;
   b) 800 mg *Echinacea purpura*:
   c) 800 mg Sage extract;
   d) 400 mg Cat's Claw extract (*Unicaria tomentsa*); and
   e) 200 mg Black Elderberry extract (*Sambucus nigra*) or 200 mg American Elderberry extract (*Sambucus canadensis*)
   f) 400 mg pomegranate extract; and
   g) 400 mg *Radix bupleuri* extract.

Example 16

16. The method as in example 15, wherein the step of administering the effective amount of anti-inflammatory phytochemicals and nutraceuticals include two or more of the following anti-inflammatory nutraceuticals:
   a) 1000 mg Omega-3 fatty acids, eicosapentanoic acid (EPA) and docosahexanoic acid (DHA); and 200 mg Alpha-lipoic acid;

and five or more of the following anti-inflammatory phytochemicals:
b) 400 mg curcumin extract with piperine;
c) 300 mg Green Tea extract;
d) 800 mg of *Boswellia serrata*, containing its most anti-inflammatory moiety, 3-acetyl-11-keto-beta-boswellic acid (AKBA);
f) 200 mg Resveratrol;
150 mg extract of Maritime pine bark extract;
400 mg *Commiphora myrrha* extract; and
400 mg *Uncaria tomentosa* extract; and
50 mg cannabidiol (CBD).

Example 17

17. A phytochemical and nutraceutical composition to prevent or limit development of virally induced infections and inflammation, including Covid-19, comprising:
an effective amount of first and second vitamins;
an effective amount of a mineral;
an effective amount of a nutraceutical and a phytochemical compound for preventing or reducing viral and bacterial infections; and an effective amount of a nutraceutical and phytochemical compound that preventing or reducing viral and bacterial inflammations.

Example 18

18. A phytochemical/nutraceutical composition as in example 17, wherein:
said first vitamin is vitamin C and said second vitamin is vitamin E;
said mineral is zinc in any of its pyrithione, citrate, gluconate, picolinate, sulfate, acetate, or orotate forms Example 19

19. A phytochemical/nutraceutical composition as in example 18, wherein:
said effective amount of a nutraceutical compound for preventing or reducing viral and bacterial infections including five or more of the following anti-infectious phytochemicals:
extracted fulvic acid; *Echinacea purpura* extract; Sage extract; *Uncaria tomentosa* extract; and Black Elderberry extract or American Elderberry extract; *Radix bupleuri* extract; pomegranate extract;

Example 20

20. A nutraceutical composition as in example 19, wherein:
said effective amount of said nutritional compound preventing or reducing viral and bacterial inflammations includes two or more of the following anti-inflammatory nutraceuticals:
Omega-3 fatty acids, eicosapentanoic acid (EPA) and docosahexanoic acid (DHA); and
Alpha-lipoic acid;
And five or more of the following anti-inflammatory phytochemicals:
Curcumin extract with piperine;
Green Tea extract;
*Boswellia serrata* extract, containing its most anti-inflammatory moiety, AKBA;
Resveratrol:
Maritime pine bark;
*Commiphora myrrha* extract, and
cannabidiol (CBD).

In a preferred embodiment, the formulary composition contains:
25 mg zinc in any of its pyrithione, citrate, gluconate, picolinate, acetate, sulfate or orotate forms, or with the cofactor methionine.
1000 mg vitamin C
200 mg vitamin E
Five or more of the following wide-spectrum anti-infectious phytochemicals:
1000 mg extracted fulvic acid
400 mg *Radix bupleuri* extract
400 mg *Uncaria tomentosa* extract
400 mg pomegranate extract
200 mg Black Elderberry extract (*Sambucus nigra*) or 200 mg American Elderberry extract (*Sambucus canadensis*);
800 mg Sage extract (*Salvia officinalis*)
800 mg *Echinacea purpura* extract
and the two anti-inflammatory nutraceuticals:
1000 mg Omega-3 fatty acids, eicosapentanoic acid (EPA) and docosahexanoic acid (DHA).
200 mg Alpha-lipoic acid and five or more of the following anti-inflammatory phytochemicals
800 mg *Boswellia serrata* extract, containing its most anti-inflammatory moiety, 3-acetyl-11-keto-β-boswellic acid (AKBA)
150 mg Maritime pine bark extract (*Pinus maritima*)
400 mg *Uncaria tomentosa* extract
400 mg *Commiphora myrrha* extract
200 mg Resveratrol
400 mg Curcumin extract with piperine
300 mg Green Tea extract
50 mg Cannabidiol (CBD)

Examples of Compositions and Methods of Second Preferred Embodiment of the Invention Example 21

21. A nutraceutical composition in capsule or other oral form for preventing or mollifying viral or bacterial infection, and also for preventing or mollifying viral or bacterial tissue inflammation consisting of:
an effective amount of vitamin C;
an effective amount of vitamin E;
an effective amount of zinc;
effective amounts of wide-spectrum anti-infectious phytochemicals; and
effective amounts of an anti-inflammatory nutraceutical and phytochemicals.

Example 22

22. The composition of example 21, wherein an effective amount of wide-spectrum anti-infectious phytochemicals include an effective amount of five or more of the following:
extracted fulvic acid; *Radix bupleuri* extract; *Echinacea purpura* extract; sage extract; pomegranate extract; *Uncaria tomentosa* extract; Black Elderberry extract or American Elderberry extract.

Example 23

23. The composition of example 21, wherein an effective amount of anti-inflammatory nutraceuticals and phytochemicals include an effective amount of two or more of the following:
Nutraceuticals Omega-3 fatty acids; eicosapentanoic acid (EPA) and docosahexanoic acid (DHA); and
five or more of the following anti-inflammatory phytochemicals:
*Boswellia serrata* extract containing 3-acetyl-11-keto-beta-boswllic acid (AKBA); Maritime pine bark extract (*Pinus maritima*); *Unicaria tomentosa* extract; *Commiphora myrrha* extract; Resveratrol; Curcumin extract with piperine; green tea extract; and Cannabidiol.

Example 24

24. The composition of example 21, wherein an effective amount of anti-infectious phytochemicals and an effective amount of anti-inflammatory nutraceuticals and phytochemicals include:
Five or more of the following anti-infectious phytochemicals:
fulvic acid extract; *Radix bupleuri* extract;
*Echinacea purpura*; sage extract; Cats Claw extract (*Uncaria tomentosa*); Black Elderberry extract or American Elderberry, pomegranate extract and
two or more of the following anti-inflammatory nutraceuticals:
Omega-3 fatty acids; eicosapentanoic acid (EPA) and docosahexanoic acid (DHA); and
Five or more of the following anti-inflammatory phytochemicals:
Curcumin extract with piperine; Green Tea extracts; *Boswellia serata* extract containing 3-acetyl-11-keto-beta-boswellic acid (AKBA); resveratrol; *Commiphora myrrha* extract; *Uncaria tomentosa*; and maritime pine bark extract.

Example 25

25. The composition of example 24, wherein:
zinc in any of its pyrithione, citrate, gluconate, picolinate, sulfate, acetate, or orotate forms.

Example 26

26. The composition of example 24, wherein:
zinc with the cofactor of methionine.

Example 27

27. The composition of example 21, wherein:
the effective amount of vitamin C is 1000 mg;
the effective amount of vitamin E is 200 mg.

Example 28

28. The composition as in example 25, wherein:
an effective amount of zinc in any of its pyrithione, citrate, gluconate, picolinate, acetate, sulfate, orotate forms is 25 mg.

Example 29

29. The composition as in example 25, consisting of:
Five or more of the following anti-infectious phytochemicals and effective amounts:
1000 mg of extracted fulvic acid;
800 mg *Echinacea purpura;*
800 mg sage extract (*Salvia officinalis*);
400 Mg Cat's Claw extract (*Uncaria tomentosa*);
200 mg Black Elderberry extract (*Sambucus nigra*) or 200 mg American Elderberry extract (*Sambucus canadensis*); 400 mg pomegranate extract; 400 mg *Radix bupleuri* extract.

Example 30

30. The composition in example 29, consisting of:
two or more of the following anti-inflammatory nutraceuticals and effective amounts:
1000 mg Omega-3 fatty acids; eicosapentanoic acid (EPA) and docosahexanoic acid (DHA); 200 mg Alpha-lopoic acid;
And five or more of the following anti-inflammatory phytochemicals:
400 mg Curcumin extract with piperine;
300 mg Green Tea extract;
800 mg of *Boswellia serrata* extract, containing its most anti-inflammatory moiety, three-acetyl-11-keto-beta-boswellic acid (AKBA);
200 mg Resveratrol;
100 mg of extract of Maritime pine bark (*Pinus maritima*);
400 mg *Commiphora myrrha* extract; and
400 mg *Unicaria tomentosa* extract.

Example 31

31. A method employing the composition recited in example 30, to prevent or limit development of virally induced infections and inflammation comprising the steps of:
a) preparing the composition of example 30 for human consumption;
b) processing composition prepared for human consumption recited in example 30 in tablet, powder, pill, capsule or liquid to be taken orally; and
c) administering the processed composition recited in example 30, to a human being periodically.

Example 32

32. A method for treating a patient having symptoms caused by a viral or bacterial infection and related inflammation, including Covid-19, comprising the step of administering a nutraceutical and phytochemical composition to the patient, said nutraceutical portion of the composition consisting of vitamin C, vitamin E, and zinc in any of its pyrithione, citrate, gluconate, picolinate, sulfate, acetate, or orotate forms and appropriate nutraceutical and phytochemical components for preventing or reducing viral and bacterial infections and inflammations, wherein an effective amount of anti-infectious phytochemicals and an effective amount of anti-inflammatory nutraceuticals and phytochemicals include five or more of the following anti-infectious phytochemicals:

e) fulvic acid; *Echinacea purpura* extract; sage extract; extract; Black Elderberry extract or American Elderberry extract; pomegranate extract; and *Radix bupleuri* extract; and two or more of the following anti-inflammatory nutraceuticals:

f) Omega-3 fatty acids; eicosapentanoic acid (EPA) and docosahexanoic acid (DHA}; and Alpha-lipoic acid; and five or more of the following anti-inflammatory phytochemicals:

g) Curcumin extract with piperine; green tea extract; *Boswellia serrata* extract, containing three-acetyl-11-keto-beta-boswellic acid (AKBA); resveratrol; *Commiphora myrrha* extract; extract; extract of maritime pine bark; green tea extract; and h) Cannabidiol (CBD).

Example 33

33. The method as in example 32, wherein, the step of adding a nutraceutical composition administering nutraceutical composition containing zinc with the cofactor of methionine.

Example 34

34. The method as in example 33, wherein the step of administering the nutraceutical composition in the effective amount of vitamin C 1000 mg; effective amount of vitamin E is 200 mg; and the effective amount of zinc is 25 mg.

Example 35

35. The method as in example 34, wherein the step of administering the effective amount of anti-infectious nutraceuticals in the composition include two or more of the following anti-infectious phytochemicals:
a) 1000 mg fulvic acid extract;
b) 800 mg *Echinacea purpura:*
c) 800 mg Sage extract;
d) 400 mg Cat's Claw extract (*Unicaria tomentsa*); and
e) 200 mg Black Elderberry extract (*Sambucus nigra*) or 200 mg American Elderberry extract (*Sambucus canadensis*)
f) 400 mg pomegranate extract; and
g) 400 mg *Radix bupleuri* extract.

Example 36

36. The method as in example 35, wherein the step of administering the effective amount of anti-inflammatory phytochemicals and nutraceuticals include two or more of the following anti-inflammatory nutraceuticals:
a) 1000 mg Omega-3 fatty acids, eicosapentanoic acid (EPA) and docosahexanoic acid (DHA); and 200 mg Alpha-lipoic acid;
and five or more of the following anti-inflammatory phytochemicals:
b) 400 mg curcumin extract with piperine;
c) 300 mg Green Tea extract;
d) 800 mg of *Boswellia serrata*, containing its most anti-inflammatory moiety, 3-acetyl-11-keto-beta-boswellic acid (AKBA);
f) 200 mg Resveratrol;

150 mg extract of Maritime pine bark extract;
400 mg *Commiphora myrrha* extract; and
400 mg *Uncaria tomentosa* extract; and
50 mg cannabidiol (CBD).

Example 37

37. A phytochemical and nutraceutical composition to prevent or limit development of virally induced infections and inflammation, including Covid-19, comprising:
an effective amount of first and second vitamins;
an effective amount of a mineral;
an effective amount of a nutraceutical and a phytochemical compound for preventing or reducing viral and bacterial infections; and an effective amount of a nutraceutical and phytochemical compound that preventing or reducing viral and bacterial inflammations.

Example 38

38. A phytochemical/nutraceutical composition as in example 37, wherein:
said first vitamin is vitamin C and said second vitamin is vitamin E;
said mineral is zinc in any of its pyrithione, citrate, gluconate, picolinate, sulfate, acetate, or orotate forms.

Example 39

39. A phytochemical/nutraceutical composition as in example 38, wherein:
said effective amount of a nutraceutical compound for preventing or reducing viral and bacterial infections including five or more of the following anti-infectious phytochemicals:
extracted fulvic acid; *Echinacea purpura* extract; Sage extract; *Uncaria tomentosa* extract; and Black Elderberry extract or American Elderberry extract; *Radix bupleuri* extract; pomegranate extract;

Example 40

40. A nutraceutical composition as in example 39, wherein:
said effective amount of said nutritional compound preventing or reducing viral and bacterial inflammations includes two or more of the following anti-inflammatory nutraceuticals:
Omega-3 fatty acids, eicosapentanoic acid (EPA) and docosahexanoic acid (DHA); and
Alpha-lipoic acid;
And five or more of the following anti-inflammatory phytochemicals:
Curcumin extract with piperine;
Green Tea extract;
*Boswellia serrata* extract, containing its most anti-inflammatory moiety, AKBA;
Resveratrol:
Maritime pine bark;
*Commiphora myrrha* extract, and
Cannabidiol (CBD).

Any of the listed wide-spectrum anti-infectious nutraceuticals and phytochemicals permutated with any of the listed anti-inflammatory nutraceuticals and phytochemicals will confer five levels of anti-infectious protection, including white blood cell fortification and activation, virucidal-bactericidal activity, enhancement of antibody production, antioxidant activity and anti-inflammatory activity. The oral formulary, capsule or other, is enteric-coated to prevent breakdown by gastric acid and permit delivery of unaltered nutraceuticals and phytochemicals to the duodenum for absorption.

The method of the invention includes the steps of providing a patient with an antiviral and/or anti-inflammatory capsule or other oral form containing a nutraceutical and phytochemical composition described herein to treat viral infections and inflammations resulting therefrom, once or more daily, in prescribed amounts, depending on the condition of the patient.

Although the present invention has been described in detail with particular reference in a preferred embodiment thereof, it should be understood that the invention is capable of other different embodiments, and its details are capable of modifications in various obvious respects. As is readily apparent to those skilled in the art, variations and modifications can be affected while remaining within the spirit and scope of the invention. Accordingly, the foregoing disclosure description is for illustrative purposes only and do not any way limit the invention which is defined only by the claims.

What is claimed is:

1. A nutraceutical composition in a capsule for preventing or mollifying viral or bacterial infection, and also for preventing or mollifying viral or bacterial tissue Inflammation, the composition comprising:
   an effective amount of vitamin C;
   an effective amount of vitamin E;
   an effective amount of zinc;
   effective amounts of wide-spectrum anti-infectious phytochemicals; and
   effective amounts of an anti-inflammatory nutraceutical and phytochemicals, wherein an effective amount of wide-spectrum anti-infectious phytochemicals include an effective amount of five or more of the following:
   extracted fulvic acid; *Radix bupleuri* extract; *Echinacea purpura* extract; sage extract; pomegranate extract; *Uncaria tomentosa* extract; Black Elderberry extract; or American Elderberry extract.

2. The composition of claim 1, wherein an effective amount of anti-inflammatory nutraceuticals and phytochemicals includes an effective amount of two or more of the following:
   Nutraceuticals Omega-3 fatty acids; eicosapentanoic acid (EPA) and docosahexanoic acid (DHA); and
   five or more of the following anti-inflammatory phytochemicals:
   *Boswellia serrata* extract containing 3-acetyl-11-keto-beta-boswellic acid (AKBA); Maritime pine bark extract; *Uncaria tomentosa* extract; *Commiphora myrrha* extract; Resveratrol;
   Curcumin extract with piperine; green tea extract; and Cannabidiol.

3. The composition of claim 1, wherein an effective amount of anti-infectious phytochemicals and an effective amount of anti-inflammatory nutraceuticals and phytochemicals include:
   five or more of the following anti-infectious phytochemicals: fulvic acid extract; *Radix bupleuri* extract; *Echinacea purpura*, sage extract; Cats Claw extract; Black Elderberry extract or American Elderberry extract; or pomegranate extract;
   two or more of the following anti-inflammatory nutraceuticals: Omega-3 fatty acids; eicosapentanoic acid (EPA); and docosahexanoic acid (DHA); and
   five or more of the following anti-inflammatory phytochemicals: Curcumin extract with piperine; Green Tea extracts; *Boswellia serrata* extract containing 3-acetyl-11-keto-beta-boswellic acid (AKBA); resveratrol; *Commiphora myrrha* extract; *Uncaria tomentosa*; and maritime pine bark extract.

4. The composition of claim 3, wherein:
   zinc is with the cofactor of methionine.

5. The composition of claim 1, wherein:
   the effective amount of vitamin C is 1000 mg; and
   the effective amount of vitamin E is 200 mg.

6. The composition of claim 3, wherein:
   the effective amount of zinc is in any of its pyrithione, citrate, gluconate, picolinate, acetate, sulfate, or orotate forms at 25 mg.

7. The composition of claim 3, the five or more of the following anti-infectious phytochemicals and effective amounts comprise:
   1000 mg of extracted fulvic acid;
   800 mg *Echinacea purpura*;
   800 mg sage extract;
   400 mg Cat's Claw extract;
   200 mg Black Elderberry extract or 200 mg American Elderberry extract;
   400 mg pomegranate extract; and
   400 mg *Radix bupleuri* extract.

8. The composition of claim 7, wherein:
   the two or more of the following anti-inflammatory nutraceuticals comprise:
   1000 mg of Omega-3 fatty acids, eicosapentanoic acid (EPA) and docosahexanoic acid (DHA);
   and
   the five or more of the following anti-inflammatory phytochemicals comprise:
   400 mg Curcumin extract with piperine;
   300 mg Green Tea extract;
   800 mg of *Boswellia serrata* extract, containing its most anti-inflammatory moiety, 3-acetyl-11-keto-beta-boswellic acid (AKBA);
   200 mg Resveratrol;
   100 mg of extract of Maritime pine bark;
   400 mg *Commiphora myrrha* extract; and
   400 mg *Unicaria tomentosa* extract.

9. A phytochemical and nutraceutical composition in capsule form to prevent or limit development of virally induced infections and inflammation, including Covid-19, the composition comprising:
   an effective amount of first and second vitamins;
   an effective amount of a mineral;
   an effective amount of nutraceuticals and phytochemicals for preventing or reducing viral and bacterial infections; and
   an effective amount of nutraceuticals and phytochemicals for preventing or reducing viral and bacterial inflammations;
   wherein said first vitamin is vitamin C and said second vitamin is vitamin E; and
   wherein said mineral is zinc in any of its pyrithione, citrate, gluconate, picolinate, sulfate, acetate, or orotate forms;
   wherein the anti-infectious nutraceuticals for preventing or reducing viral and bacterial infections include five or more of the following: extracted fulvic acid; *Echinacea purpura* extract; Sage extract; *Uncaria tomentosa* extract; Black Elderberry extract or American Elderberry extract; *Radix bupleuri* extract; or pomegranate extract.

10. The composition of claim 9,
wherein said nutraceuticals for preventing or reducing viral and bacterial inflammations include two or more of the following:
   Omega-3 fatty acids, eicosapentanoic acid (EPA) and docosahexanoic acid (DHA); and Alpha-lipoic acid; and
wherein said anti-inflammatory phytochemicals include five or more of the following:
   Curcumin extract with piperine;
   Green Tea extract;
   *Boswellia serrata* extract, containing its most anti-inflammatory moiety, AKBA;
Resveratrol:
Maritime pine bark;
*Commiphora myrrha* extract; and
cannabidiol (CBD).

11. A composition in oral tablet form comprising:
an effective amount of vitamin C;
an effective amount of vitamin E;
an effective amount of zinc, wherein zinc is in any of its pyrithione, citrate, gluconate, picolinate, sulfate, acetate, or orotate forms or complexed with methionine;
effective amounts of wide-spectrum anti-infectious phytochemicals for preventing or mollifying viral or bacterial infection; and
effective amounts of an anti-inflammatory nutraceutical and phytochemicals for preventing or mollifying viral or bacterial inflammation; and enveloped by an enteric coating;
wherein the wide spectrum anti-infectious phytochemicals comprise five or more of the following: fulvic acid extract; *Radix bupleuri* extract; *echinacea* extract; sage extract; Cat's Claw extract; Black Elderberry extract or American Elderberry extract, or pomegranate extract;
wherein the anti-inflammatory nutraceutical comprises EPA, DHA, or a combination thereof; and
wherein the anti-inflammatory phytochemicals comprise five or more of the following:
Curcumin extract with piperine; Green Tea extract; *Boswellia serrata* extract containing 3-acetyl-11-keto-beta-boswellic acid (AKBA); resveratrol; *Commiphora myrrha* extract; Cat's Claw extract; and pine bark extract.

12. A composition in parenteral form for preventing or mollifying viral or bacterial infection, and also for preventing or mollifying viral or bacterial tissue inflammation, the composition comprising:
an effective amount of vitamin C;
an effective amount of vitamin E;
an effective amount of zinc, wherein zinc is in any of its pyrithione, citrate, gluconate, picolinate, sulfate, acetate, or orotate forms or complexed with methionine;
effective amounts of wide spectrum anti-infectious phytochemicals; and
effective amounts of anti-inflammatory nutraceuticals and phytochemicals;
wherein the wide-spectrum anti-infectious phytochemicals comprise five or more of the following: fulvic acid extract; *Radix bupleuri* extract; *echinacea* extract; sage extract; Cat's Claw extract; Black Elderberry extract or American Elderberry; and pomegranate extract;
wherein the anti-inflammatory nutraceuticals include EPA, DHA or combination thereof; and
wherein the anti-inflammatory phytochemicals include five or more of the following: curcumin extract with piperine; Green Tea extract; *Boswellia serrata* extract; resveratrol; *Commiphora myrrha* extract; Cats Claw extract; and pine bark extract.

\* \* \* \* \*